United States Patent [19]

Marti et al.

[11] 4,165,268
[45] Aug. 21, 1979

[54] PROCESS FOR THE PRODUCTION OF SUBSTITUTED TOLUENE COMPOUNDS

[75] Inventors: Franz Marti, Dornach; Tibor Somlo, Birsfelden; Jacques Gosteli, Basel, all of Switzerland

[73] Assignee: Ciba-Geigy AG, Basel, Switzerland

[21] Appl. No.: 846,876

[22] Filed: Oct. 31, 1977

[30] Foreign Application Priority Data

Nov. 9, 1976 [CH] Switzerland .................. 14096/76

[51] Int. Cl.$^2$ ............................................. B07J 1/10
[52] U.S. Cl. ......................... 204/163 R; 204/158 HA
[58] Field of Search ..................... 204/158 HA, 163 R

[56] References Cited

U.S. PATENT DOCUMENTS

3,993,704  11/1976  Marsh et al. .................. 260/646

*Primary Examiner*—Leland A. Sebastian
*Attorney, Agent, or Firm*—Prabodh I. Almaula

[57] ABSTRACT

A process for the production of benzal bromides which contain an electrophilic substituent in the ortho- and/or para-position of the formula (Ia), or of mixtures thereof with the corresponding benzyl bromides of the formula (Ib),

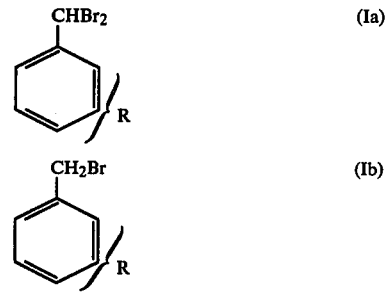

in which R represents an electrophilic substituent in the ortho- and/or para position, by treating correspondingly substituted toluenes with elementary bromine under irradiation with visible light in a two-phase system which consists of an aqueous and an organic phase, which process comprises carrying out the reaction in the presence of a base.

11 Claims, No Drawings

PROCESS FOR THE PRODUCTION OF SUBSTITUTED TOLUENE COMPOUNDS

It is known that it is exceedingly difficult to obtain benzal or benzyl halides which contain an electrophilic substituent in the ortho- and/or para-position. The side-chain halogenation, in particular the side-chain bromination, of alkyl aromatic compounds with elementary bromine requires in some cases high temperatures, which, in view of the low thermal stability of the aralkyl bromides, are disadvantageous. Compounds which are difficult to substitute, for example nitrotoluenes, are reacted in a bomb tube or pressure flask at 100°–160° C. (Houben-Weyl, Vol. 5/4, pp. 334–337).

Even the side-chain brominations of o-nitrotoluene in a carbon tetrachloride/water mixture using elementary bromine and under UV-irradiation, which have been described recently in German Democratic Republic patent specifications Nos. 74279 and 82463, provide only o-nitrobenzyl bromide in a yield of 45 to 55%. Continuation of the bromination did not prove advantageous. The process described in German Democratic Republic patent specification No. 118609 affords a somewhat better yield when o-nitrotoluene is brominated in carbon tetrachloride under irradiation with visible or ultra-violet light or using peroxide as catalyst; but in this process too it was not possible to obtain either a benzal bromide or a complete bromination of o-nitrotoluene as starting material to benzyl bromide.

The invention provides a novel process for the production of benzal bromides which contain in the ortho- and/or para-position an electrophilic substituent, or mixtures thereof with the corresponding benzyl bromides, of the general formulae

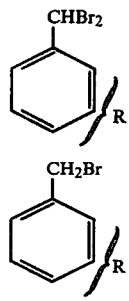

in which R represents an electrophilic substituent in the ortho- and/or para-position, by treating correspondingly substituted toluenes with elementary bromine under irradiation with visible light in a two-phase system which consists of an aqueous and an organic phase, which process comprises carrying out the reaction in the presence of a base.

Electrophilic substituents R are for example the nitro group, the cyano group or a halogen atom, for example chlorine, bromine, iodine or fluorine.

Hitherto, a base had not been used during the bromination, because it was known from Houben-Weyl that the benzyl/benzal bromides in aqueous/alkaline solution readily saponify to aldehydes, alcohols and by-products (Cannizzaro reaction). It is all the more surprising that, in the presence of bases, no saponification takes place and the desired brominated products are obtained in good yield and purity.

As bases it is possible to use metallic bases, for example alkali metal or alkaline earth metal bases which contain a hydroxyl, hydrogen carbonate or carbonate ion, or anion exchangers in hydroxyl ion form, for example Dowex 2 ® (quaternary ammonium hydroxides).

In particular, it is possible to use sodium or potassium hydroxide, sodium or potassium hydrogen carbonate or sodium or potassium carbonate.

In analogous manner, the corresponding hydroxides, hydrogen carbonates and carbonates of calcium and magnesium can be used as bases. The reaction is carried out using a readily soluble base, for example an alkali base, preferably in a pH range between 7.5 and 11 at a temperature between 30° and 90° C., preferably in the presence of an organic phase consisting of an inert and as far as possible apolar solvent. If the reaction is carried out in the presence of a sparingly soluble base, for example an alkaline earth carbonate, for example calcium carbonate, then the pH value falls below 7.5 to about 4. Halogenated aromatic hydrocarbons, for example chloro or bromobenzenes, and also nitrobenzenes, as well as carbon disulphide or halogenated alkanes, preferably carbon tetrachloride, methylene chloride or chloroform, can be used in particular as inert and as far as possible apolar solvents.

When using more than the two-fold amount of bromine and increasing the bromination time, primarily benzal bromide is obtained. However, when using only about one and a half times the molar amount of bromine, then primarily a mixture of benzal and benzyl bromide is obtained. An increase of the pH range beyond the indicated range of 7.5 to 11 promotes the undesired increase of metallic bromate from the resultant metal hypobromite as a result of disproportionation. As stated above, the bromination is carried out under irradiation with visible light, i.e., in the range between 3800 and 8000 Å. Suitable sources of light for the process of the invention are tungsten lamps, for example incandescent filaments or fluorescent tubes, with which glass vessels can be irradiated externally, or immersion lamps for visible light, which can be built into metallic reaction vessels are used. In order to prevent losses of light and heat in glass vessels, it is advantageous to provide a jacket of aluminium foil which reflects light. Constant stirring of the reaction mixture is most advantageous to achieve a better mixing of the two-phase system.

Compared with the cited prior art, i.e. with German Democratic Republic patent specifications Nos. 7427, 82463 and 118609, the following advantages accrue:

1. The bromination in the presence of a base in a two-phase system which consists of an aqueous phase and an organic phase yields benzal bromide, depending on the amount of bromine added and the time, or, in the case of an ortho-substituent, a mixture of benzal bromide and the corresponding benzyl bromide without a trace of unreacted starting material. Also, no tribromide forms during this reaction.
2. Depending on how the process conditions are varied, it is possible to obtain a 10 to 30% increase in yield of reacted toluene using the described process.
3. No hydrogen bromide escapes owing to the presence of the base, since the former is neutralised by the base, accompanied by salt formation.
4. The bromides of the bases obtained, preferably the metal bromides, for example the alkali or alkaline earth bromides, are in directly reusable form, since the elementary bromine can be recovered by regeneration in an exceedingly simple manner.

The benzyl bromides obtained by the process of the present invention can be used as intermediates for the production of the corresponding benzaldehydes. In addition, the mixture of o-substituted benzyl and benzal bromides can be converted, according to the invention, into a mixture consisting of the formate of the corresponding benzyl alcohol and the corresponding benzaldehyde by addition of an alkali formiate. This mixture can be converted by hydrolysis and subsequent oxidation with aqueous nitric acid to give the pure benzaldehyde.

The o-nitrobenzaldehyde which can be obtained from o-nitrobenzal bromide, or from the mixture of o-nitrobenzyl or o-nitrobenzal bromide, is a useful intermediate and can be used, for example, for the indigo synthesis of A. v. Baeyer. o-Nitrobenzaldehyde is also used as a diagonstic agent in medicine, for example in diabetes.

o-Cyanobenzyl bromide and/or o-cyanobenzal bromide can be used for the preparation of o-cyanobenzaldehyde. o-Cyanobenzaldehyde is used as an intermediate for the preparation of anti-hypertensive pharmaceutical preparations with coronary dilating and peripherally dilating action (cf. German Offenlegungsschrift No. 1,963,188) and as starting product for the preparation of o-cyanocinnamic acids which are important for pharmaceutical syntheses. In addition, o-cyanobenzaldehyde is used as a stabilising additive for methyl chloroform (cf. U.S. patent specification No. 3,364,270) and as additive for fibres containing polyvinyl alcohol to improve their elasticity and dyeability (cf. U.S. Pat. No. 3,071,429).

The invention is illustrated by the following Examples, in which the parts are by weight.

EXAMPLE 1

68.5 g (0.5 mole) of o-nitrotoluene are dissolved in 660 ml of carbon tetrachloride in a 1.5 liter sulphonating flask and 50 ml of water are added. With stirring, the reaction flask is irradiated from below with a 200 watt tungsten lamp and thereby simultaneously heated. After reflux temperature (69° C.) of the azeotropic mixture has been attained, elementary bromine is added in such a manner that the solution always just becomes decolourised. The pH value is simultaneously kept constant at 7.5 with sodium hydroxide solution. The bromination is interrupted after 2 hours and 50 minutes, the phases are separated and the organic phase is washed with water, dried over sodium sulphate and concentrated, affording 55 g of o-nitrobenzyl bromide (51%) and 72.3 g of o-nitrobenzal bromide (49%). The consumption of bromine is 107% of theory, that of NaOH approx. 120% of theory.

EXAMPLE 2

68.5 g (0.5 mole) of o-nitrotoluene are brominated as described in Example 1 for 15 hours. After working up, 145 g of o-nitrobenzal bromide are isolated (98%). The consumption of bromine is 137% of theory, that of NaOH 170% of theory. The structure is confirmed by NMR spectroscopy. The melting point is 60° C. and the bromine content determined by mass analysis is in accordance with theory.

EXAMPLE 3

68.5 g (0.5 mole) of o-nitrotoluene are dissolved in 400 ml of methylene chloride and bromination is carried out as described in Example 1 for 6 hours at 40° C. The pH value is kept constant at 7.5 with 20% aqueous sodium carbonate solution. Yield: 74.5 g of o-nitrobenzyl bromide (69%) and 45.7 g of o-nitrobenzal bromide (31%). The bromine consumption is 170% of theory.

EXAMPLE 4

68.5 g (0.5 mole) of o-nitrotoluene are brominated as described in Example 3 for 20 hours at 40° C. Yield: 144.5 g of o-nitrobenzal bromide (98%). The Bromine consumption is about 200% of theory.

EXAMPLE 5

68.5 g (0.5 mole) of p-nitrotoluene are dissolved in 400 ml of carbon tetrachloride and bromination is effected as described in Example 1 for 1 hour, affording 10.3 g (15%) of unreacted starting material, 70.2 g of p-nitrobenzyl bromide (65%) and 29.5 g (20%) of p-nitrobenzal bromide. The bromine consumption is 110% of theory and the consumption of NaOH is 120% of theory.

EXAMPLE 6

63.2 g (0.5 mole) of o-chlorotoluene are brominated for 60 minutes as described in Example 5, affording 51.4 g of o-chlorobenzyl bromide (50%) and 71.1 g (50%) of o-chlorobenzal bromide. The consumption of bromine and NaOH corresponds to theory.

EXAMPLE 7

63.2 g (0.5 mole) of o-chlorotoluene are brominated for 4 hours as described in Example 5, affording 142.3 g of o-chlorobenzal bromide (100%). The bromine consumption is 108% of theory, the NaOH consumption 110% of theory.

EXAMPLE 8

55.1 g (0.47 mole) of p-cyanotoluene are brominated as in Example 5 and the reaction mixture is worked up after 3 hours and 20 minutes, affording 5.5 g of unreacted starting material (10%), 70 g (76%) of p-cyanobenzyl bromide and 18.1 g (14%) of p-cyanobenzal bromide. The bromine consumption is 115% of theory and the NaOH consumption is 130% of theory.

EXAMPLE 9

68.5 g of o-nitrotoluene are dissolved in 400 ml of carbon tetrachloride. Then 100 ml of water and 55 g of calcium carbonate are added and bromination is effected in such a manner that the mixture always just becomes decolourised. Yield: 48.6 g (45%) of o-nitrobenzyl bromide and 81.1 g (55%) of o-nitrobenzal bromide. The bromine consumption is 106% of theory.

EXAMPLE 10

58.5 g (0.5 mole) of o-cyanotoluene are dissolved in 636 g (400 ml) of carbon tetrachloride and the solution, after addition of 100 ml of water, is heated to reflux temperature and then brominated under irradiation with a 150 watt sodium high pressure lamp in such a manner that the bromine is always just consumed. Simultaneously, the pH value is kept constant at 7.8 with 20% sodium hydroxide solution. After addition of 184 g (115% of theory) of bromine and a consumption of 260 g of 20% sodium hydroxide solution, the organic phase is separated and the aqueous layer is extracted with carbon tetrachloride. Yield: 135 g of o-cyanobenzal bromide with a content of 98%.

What is claimed is:

1. A process for the production of benzal bromides which contain an electrophilic substituent in the ortho- or para-position of the formula (Ia), or of mixtures thereof with the corresponding benzyl bromides of the formula (Ib),

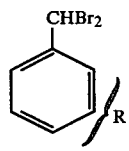
(Ia)

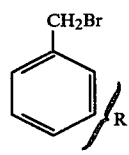
(Ib)

in which R represents an electrophilic substituent in the ortho- or para-position, by treating correspondingly substituted toluenes with elementary bromine under irradiation with visible light in a two-phase system which consists of an aqueous and an organic phase, which process comprises carrying out the reaction in the presence of a base.

2. A process according to claim 1 wherein the bromination is carried out in the presence of a metallic base.

3. A process according to claim 1 wherein the bromination is carried out in the presence of an alkali metal base or an alkaline earth metal base.

4. A process according to claim 1 wherein the bromination is carried out in the presence of a soluble alkali metal hydroxide or alkaline earth metal hydroxide at a pH value higher than 7.

5. A process according to claim 1 wherein the bromination is carried out in the presence of soluble sodium hydroxide or calcium hydroxide at a pH value higher than 7.

6. A process according to claim 1 wherein the bromination is carried out in the presence of an alkali metal carbonate or alkaline earth metal carbonate.

7. A process according to claim 1 wherein the bromination is carried out in the presence of sodium carbonate or calcium carbonate.

8. A process according to claim 1 wherein the bromination is carried out in the presence of a readily soluble base cited in claim 1 and in a pH range between 7.5 and 11.

9. A process according to claim 1 wherein the bromination is carried out in the presence of a sparingly soluble base cited in claim 1 at a pH value higher than 4.

10. A process according to claim 1 wherein the bromination is carried out at a temperature between 30° and 90° C.

11. A process according to claim 1 wherein the bromination is carried out using a tungsten lamp as source of visible light.